(12) United States Patent
Hendrikse et al.

(10) Patent No.: US 9,972,482 B2
(45) Date of Patent: May 15, 2018

(54) CONCENTRIC APCI SURFACE IONIZATION ION SOURCE, ION GUIDE, AND METHOD OF USE

(71) Applicant: Smiths Detection Montreal Inc., Mississauga (CA)

(72) Inventors: Jan Hendrikse, Whitby (CA); Vladimir Romanov, Vaughan (CA)

(73) Assignee: Smiths Detection Montreal Inc., Mississauga, Ontario (CA)

( * ) Notice: Subject to any disclaimer, the term of this patent is extended or adjusted under 35 U.S.C. 154(b) by 0 days. days.

(21) Appl. No.: 15/634,151

(22) Filed: Jun. 27, 2017

(65) Prior Publication Data

US 2017/0365455 A1   Dec. 21, 2017

Related U.S. Application Data

(63) Continuation of application No. 15/036,433, filed as application No. PCT/CA2014/051095 on Nov. 14, 2014, now Pat. No. 9,728,389.

(60) Provisional application No. 61/904,794, filed on Nov. 15, 2013.

(51) Int. Cl.
| | |
|---|---|
| *H01J 49/16* | (2006.01) |
| *H01J 49/14* | (2006.01) |
| *H01J 49/00* | (2006.01) |
| *H01J 49/24* | (2006.01) |
| *H01J 49/04* | (2006.01) |

(52) U.S. Cl.
CPC ........ *H01J 49/168* (2013.01); *H01J 49/0022* (2013.01); *H01J 49/0036* (2013.01); *H01J 49/0404* (2013.01); *H01J 49/145* (2013.01); *H01J 49/24* (2013.01)

(58) Field of Classification Search
USPC .................................. 250/288, 281, 282
See application file for complete search history.

(56) References Cited

U.S. PATENT DOCUMENTS

| | | | | |
|---|---|---|---|---|
| 5,285,064 | A * | 2/1994 | Willoughby | .......... H01J 49/049 250/283 |
| 5,416,322 | A | 5/1995 | Chace et al. | |
| 5,736,740 | A | 4/1998 | Franzen | |
| 5,750,988 | A | 5/1998 | Apffel et al. | |
| 8,502,140 | B2 | 8/2013 | Whitehouse et al. | |
| 9,063,047 | B2 * | 6/2015 | Van Berkel | .......... G01N 1/4055 |

(Continued)

OTHER PUBLICATIONS

International Search Report dated Feb. 3, 2015 for PCT/CA2014/051095.

*Primary Examiner* — Kiet T Nguyen
(74) *Attorney, Agent, or Firm* — Advent, LLP (57) ABSTRACT

A concentric APCI surface ionization probe, supersonic sampling tube, and method for use of the concentric APCI surface ionization probe and supersonic sampling tube are described. In an embodiment, the concentric APCI surface ionization probe includes an outer tube, an inner capillary, and a voltage source coupled to the outer tube and the inner capillary. The inner capillary is housed within and concentric with the outer tube such that ionized gas (e.g., air) travels out of the outer tube, reacts with a sample, and the resulting analyte ions are sucked into the inner capillary. A supersonic sampling tube can include a tube coupled to a mass spectrometer and/or concentric APCI surface ionization probe, where the tube includes at least one de Laval nozzle.

7 Claims, 13 Drawing Sheets

(56) References Cited

U.S. PATENT DOCUMENTS

| | | |
|---|---|---|
| 2006/0255261 A1 | 11/2006 | Whitehouse et al. |
| 2007/0023631 A1 | 2/2007 | Takats et al. |
| 2011/0036978 A1 | 2/2011 | Franzen |
| 2012/0312980 A1 | 12/2012 | Whitehouse |
| 2013/0299688 A1* | 11/2013 | Balogh ................ H01J 49/168 250/282 |

* cited by examiner

CONCENTRIC APCI SURFACE IONIZATION ION SOURCE, ION GUIDE, AND METHOD OF USE

This application claims the benefit of U.S. Provisional Application No. 61/904,794, filed Nov. 15, 2013, the contents of which are incorporated herein by reference in their entirety.

BACKGROUND

Mass spectrometers (MS) operate in a vacuum and separate ions with respect to mass-to-charge ratio. In some embodiments using a mass spectrometer, a sample, which may be solid, liquid, or gas, is ionized. The ions are separated in a mass analyzer according to mass-to-charge ratio and are detected by a device capable of detecting charged particles. The signal from a detector in the mass spectrometer is then processed into spectra of the relative abundance of ions as a function of the mass-to-charge ratio. The atoms or molecules are identified by correlating the identified masses with known masses or through a characteristic fragmentation pattern.

SUMMARY

A concentric atmospheric-pressure chemical ionization (APCI) surface ionization probe, supersonic sampling tube, and method for use of the concentric APCI surface ionization probe and supersonic sampling tube are described. In an embodiment, the concentric APCI surface ionization probe includes an outer tube configured to function as a first electrode, an inner capillary configured to function as a second electrode, and a voltage source coupled to the outer tube and the inner capillary. The inner capillary is housed within and concentric with the outer tube such that ionized gas (e.g., air) travels out of the outer tube, reacts with a sample, and the resulting analyte ions are sucked into the inner capillary. Additionally, a supersonic sampling tube can include a tube coupled to a mass spectrometer and/or concentric APCI surface ionization probe, where the tube includes at least a first de Laval nozzle. A buffered plug of ions travels at a supersonic speed through the tube after the first de Laval nozzle, which prevent sticking of the ions in the buffered plug of ions to the side of the tube. In some implementations, a second de Laval nozzle can slow down the flow of the buffered plug of ions to subsonic speed. In an implementation, a process for utilizing the concentric APCI surface ionization probe and supersonic sampling tube that employs the techniques of the present disclosure includes scanning a surface, using a concentric APCI surface ionization probe, for molecules indicating the presence of at least one fingerprint; indicating a positive signal when at least one fingerprint is detected; and scanning the surface, using a concentric APCI surface ionization probe, for at least one explosive.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. The use of the same reference number in different instances in the description and the figures may indicate similar or identical items.

DETAILED DESCRIPTION

Mass spectrometers (MS) operate in a vacuum and separate ions with respect to the mass-to-charge ratio. In some embodiments using a mass spectrometer, a sample, which may be solid, liquid, or gas, is ionized and analyzed. The ions are separated in a mass analyzer according to mass-to-charge ratio and are detected by a detector capable of detecting charged particles. The signal from the detector is then processed into the spectra of the relative abundance of ions as a function of the mass-to-charge ratio. The atoms or molecules are identified by correlating the identified masses with known masses or through a characteristic fragmentation pattern.

Portable mass spectrometer systems have limitations on sample introduction methods into a vacuum manifold because of the smaller pumping systems (most commonly effluent from gas chromatography capillary or flow through a permeable membrane are used). The range of analytes which can be efficiently examined is thereby limited by the sample introduction and ionization methods employed. One type of portable mass spectrometry includes surface ionization, which involves the creation of ions proximate to an ion source. The current geometry of surface ionization sources works well for lab-based instruments when the surface to be analyzed can be brought close to the ion source. However, it may become awkward when large objects to be scanned and tested need to be brought proximate to a mass spectrometer.

Often, a surface ionization source is coupled to the mass spectrometer unit by a sampling tube. Ions are transported down the sampling tube in the gas flow from the outside atmosphere to the mass spectrometer vacuum. Sometimes, this can result in ion losses to the inner walls of the tube. Further losses of ions to the walls of the tube result when the transfer time of the gas through the tube is sufficiently long for the analyte ions to diffuse or migrate to the tube wall.

Figure 2:
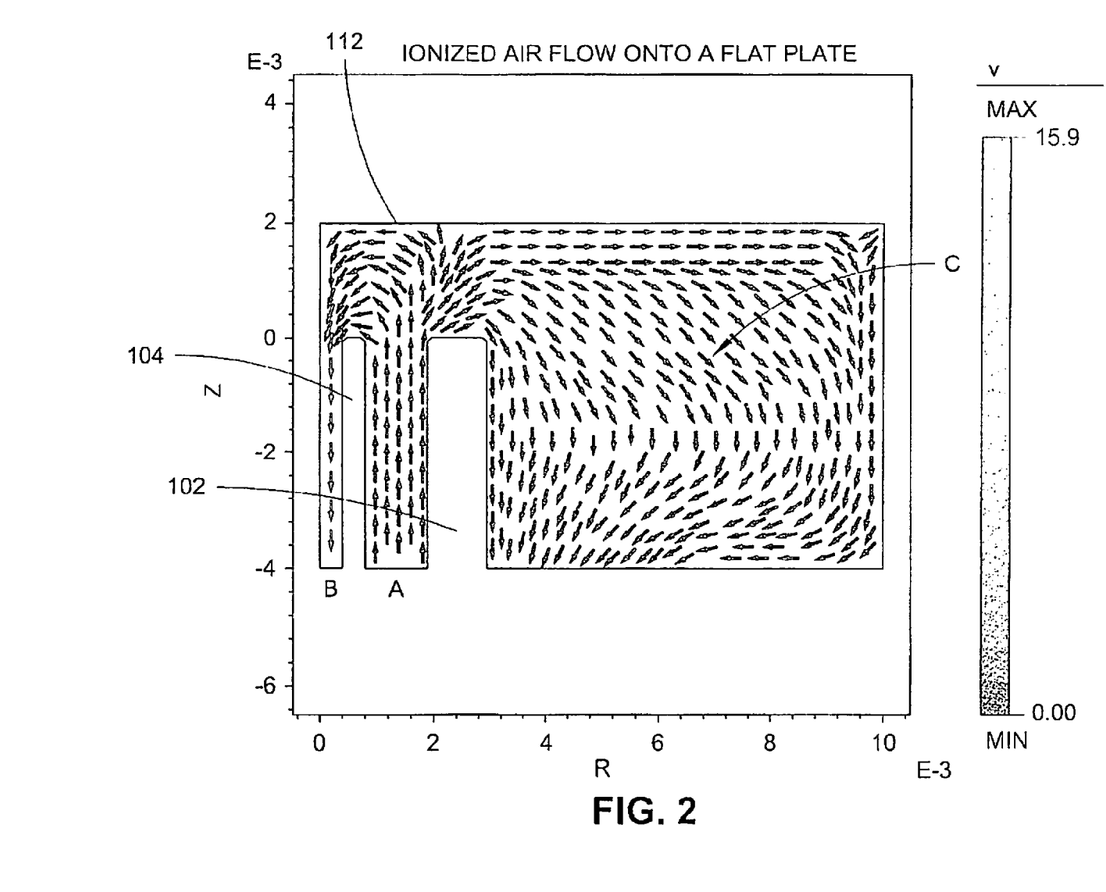
FIG. 2 is a diagrammatic view illustrating an ionized gas flow field when a concentric APCI surface ionization probe is placed proximate to a surface in accordance with an example implementation of the present disclosure.

Accordingly, a concentric APCI surface ionization probe, supersonic sampling tube, and method for use of the concentric APCI surface ionization probe and supersonic sampling tube are described. In an embodiment, the concentric APCI surface ionization probe includes an outer tube configured to function as a first electrode, an inner capillary configured to function as a second electrode, and a voltage source coupled to the outer tube and the inner capillary. The inner capillary is housed within and concentric with the outer tube such that ionized gas (e.g., air) travels out of the outer tube, reacts with a sample, and the resulting analyte ions are sucked into the inner capillary. The inner capillary electrode is configured in such a way that the gas is ionized away from the inner capillary and close to the inner wall of the outer tube. The ions formed at this position are transported to the center of the inner capillary inlet, while the gas passing close to the outside of the inner capillary is transported to the inside wall of the capillary, as indicated in FIG. 2. This process thus creates a central plug of ions inside the capillary, surrounded by a sheath of air that was not ionized. This plug of ions and its surrounding gas may be referred to as a buffered plug of ions. It will be clear to one skilled in the art that the formation of the buffered plug of ions is driven by the gas flow field. In fact, if the needle electrode is placed sufficiently far away from the capillary tip, there will be a region between the position where the ions are created and the probe tip where the electric field between the inner and outer electrodes does not drive the ions towards the probe exit at all. Additionally, a supersonic sampling tube can include a tube coupled to a mass spectrometer and/or concentric APCI surface ionization probe, where the tube includes at least a first de Laval nozzle. A buffered plug of ions travels at a supersonic speed through the tube after the first de Laval nozzle, which prevents sticking of the ions in the buffered plug of ions to the side of the tube. In some implementations, a second de Laval nozzle can slow down the flow of the buffered plug of ions to subsonic speed. In an implementation, a process for utilizing the concentric APCI surface ionization probe and supersonic sampling tube that employs the techniques of the present disclosure includes scanning a surface, using a concentric APCI surface ionization probe, for molecules indicating the presence of at least one fingerprint; indicating a positive signal when at least one fingerprint is detected; and scanning the surface, using a concentric APCI surface ionization probe, for at least one explosive.

Some advantages of the concentric low temperature plasma probe, supersonic sampling tube, and method for use of the concentric low temperature plasma probe include that the concentric geometric design provides a more compact source that can be scanned across surfaces, and ions created close to the outer tube electrode can travel further away from the probe before they are sucked into the central tube, allowing the probe to be held further away from the surface to be interrogated.

When using the concentric low temperature plasma probe, analyte ions are directed to the center of the gas flow and propelled by the gas flow in the outer tube and the inner capillary, surrounded by a sheath of clean air. This minimizes ion losses on the tube wall because most ions will reach the end of the tube before the can diffuse to the tube wall. Because of this potential diffusion to the tube walls, it is important to move the ions through the tube(s) rapidly. Preventing analyte ion losses to the tube wall is important because those ions that are lost to the tube wall do not reach the mass spectrometer, and memory effects caused by the reionization of neutralized ions that have settled on the tube wall can interfere with accurate analysis.

Figure 1:
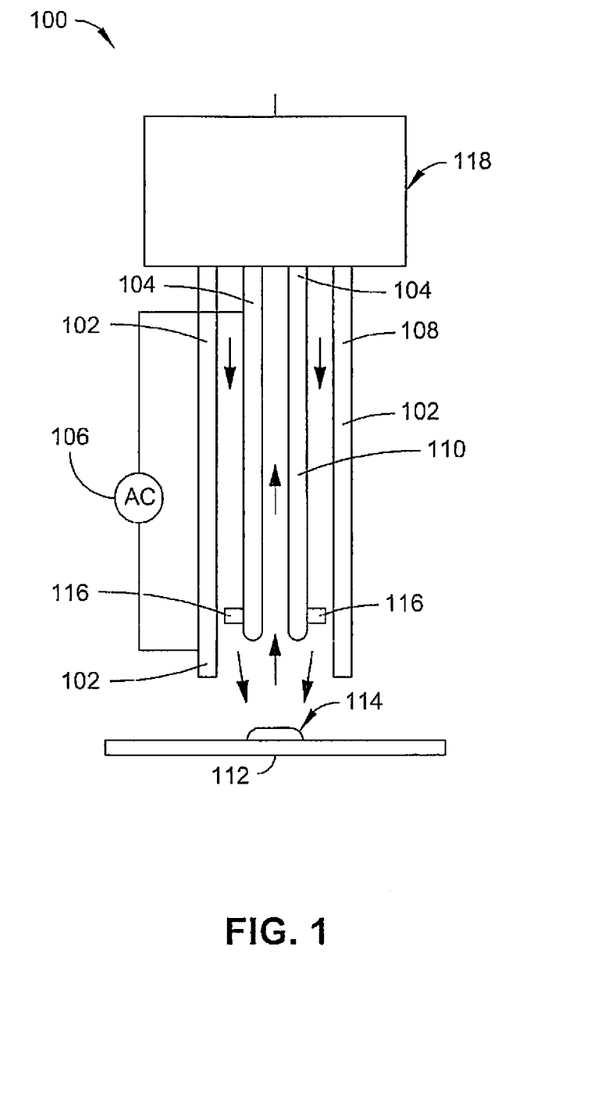
FIG. 1 is a diagrammatic cross-sectional view illustrating a concentric APCI surface ionization probe in accordance with an example implementation of the present disclosure.

FIG. 1 illustrates a concentric APCI surface ionization probe 100 in accordance with example implementations of the present disclosure. As shown, the concentric APCI surface ionization probe 100 includes an outer tube 102, an inner capillary 104, and a voltage source 106. In some implementations, the outer tube 102 may include a material that is a suitable electrical conductor. A suitable electrical conductor can function to apply a potential to an inner needle electrode 116, which in turn can form ions in the gas pumped through the outer tube. In other implementations, the outer tube 102 can be a poor electrical conductor (e.g., a dielectric) partially covered by a conductor on the outside of the tube.

Further shown in FIG. 1, the concentric APCI surface ionization probe 100 includes an inner capillary 104 housed within and concentric with the outer tube 102. Additionally, the inner capillary 104 can include at least one inner needle electrode 116. When an electrical potential is applied to a first electrode (e.g. the outer tube 102 or other electrode) and a second electrode (e.g., the inner capillary 104 or other electrode), ions can be formed from gas (e.g., air, etc.) passing through the outer tube 102. In some implementations, the inner capillary 104 may include an inner needle electrode 116. In this embodiment, an inner needle electrode 116 can include a ring with radial spikes extending outward from the ring. The ring may be configured to fit around the inner capillary 104. In one specific embodiment, the inner needle electrode 116 is in the shape of a star, with radial spikes extending outward. In other specific embodiments, the inner needle electrode 116 can be in the shape of a flat square or a gear with radial spikes and/or corners extending outward. At the tips of these spikes and/or corners, magnitude in the electrical field may be the highest, where ions can be formed from the gas in the outer tube 102. In implementations, the inner capillary 104 can include a rounded outer tip at the location where a flow of analyte ions enters the inner capillary 104 to ensure that ions are produced preferentially at the tip of needle electrode 116.

The concentric APCI surface ionization probe 100 includes a voltage source 106 coupled to a first electrode (e.g. the outer tube 102 or other electrode) and a second electrode (e.g., the inner capillary 104 or other electrode) for providing an electric potential. The electric potential creates an electric field, which creates ions in the gas in the outer tube 102 when it is sufficiently large. The concentric APCI surface ionization probe 100 can be coupled to a capillary interface 118, which can include equipment and/or plumbing to supply gas pumped through the outer tube 102, equipment and/or plumbing to couple the inner capillary 104 to analysis equipment, such as a mass spectrometry system 200. In one specific embodiment, the capillary interface 118 can include a supersonic sampling tube 202, such as that described below.

FIG. 2 illustrates an ionized gas (e.g., air, etc.) flow field when a concentric APCI surface ionization probe 100 is placed proximate (e.g., 1-3 times the diameter of the concentric APCI surface ionization probe 100) to a surface 112. As oriented in FIG. 2, a gas flow can be applied such that gas flow in the outer tube 102 is relatively slow and upwards (A), and the flow in the inner capillary 104 is fast and downward (B), especially close to the tube axis (e.g., R=0). In this surface ionization mode using a concentric APCI surface ionization probe 100, the volume flow out of the outer tube 102 is configured to be roughly equal to the flow into the inner capillary 104 so that the flow into the environment in area (C) is close to zero. In some implementations, a slightly higher gas flow into the inner capillary 104 can ensure that the ions generated in the outer tube 102 do not escape into the environment. In some embodiments, the concentric APCI surface ionization probe 100 can be used in vapor sampling mode. In this mode, the gas flow into the inner capillary 104 may be significantly larger than the gas flow out of the outer tube 102 so that there is a net flow from the surrounding area to the inner capillary 104. In one specific implementation, an oscillating gas flow can be superimposed on the gas flow through the inner capillary 104 such that the total flow is periodically reversed. In this specific implementation, the total gas flow averaged over a complete oscillation flows away from the sample and toward the mass spectrometer 212 and/or analysis system.

Figure 3:
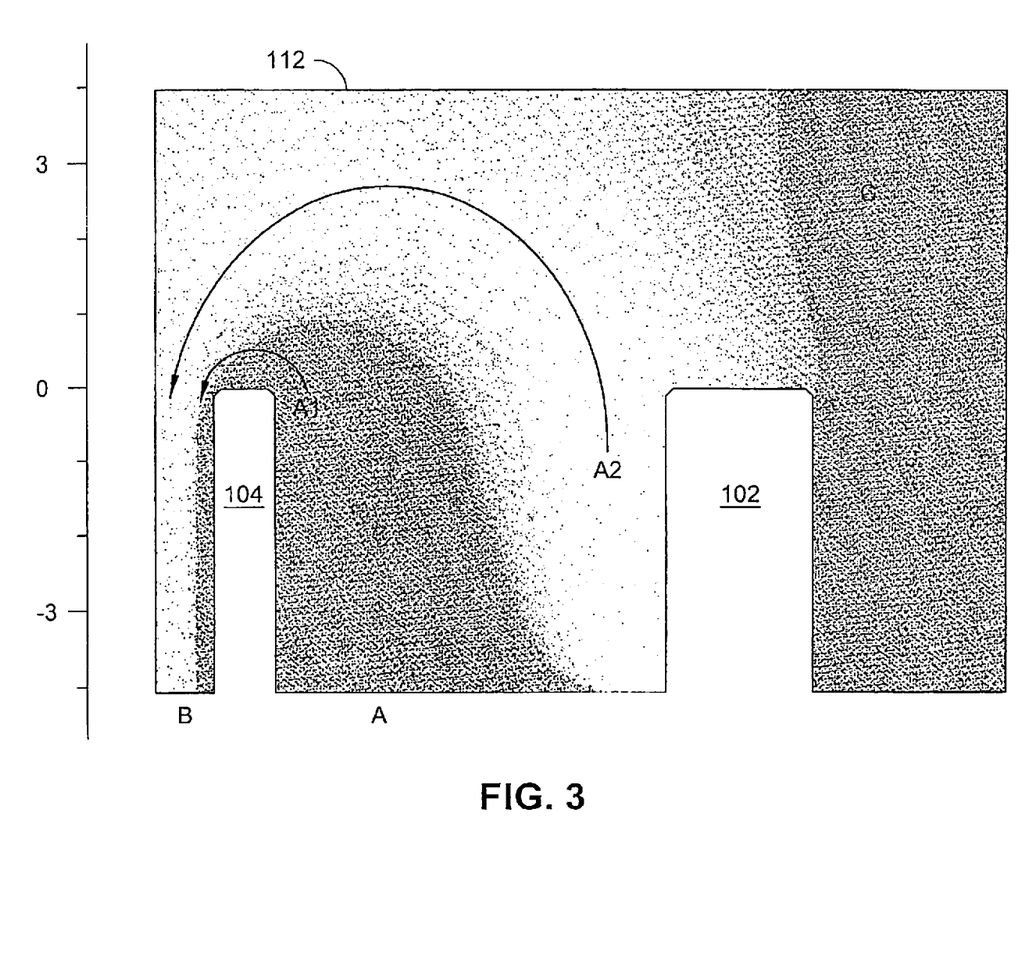
FIG. 3 is a diagrammatic view illustrating a concentration profile of ions generated by a source that generates ions in accordance with an example implementation of the present disclosure.

FIG. 3 illustrates a concentration profile of ions generated by a source that generates ions in region A2. Gas flow at position A1, close to the inner capillary 104, will likely take an inner trajectory into the inner capillary 104 without ever reaching a sample and provide a sheath of gas between the analyte ions and the inner capillary 104 wall. Ions generated in position A2, close to the outer tube 102, may likely take an outer trajectory and react with a sample present on surface 112. This ion concentration profile allows more efficient operation of a concentric APCI surface ionization probe 100 when it is not proximate to a surface 112.

Figure 4:
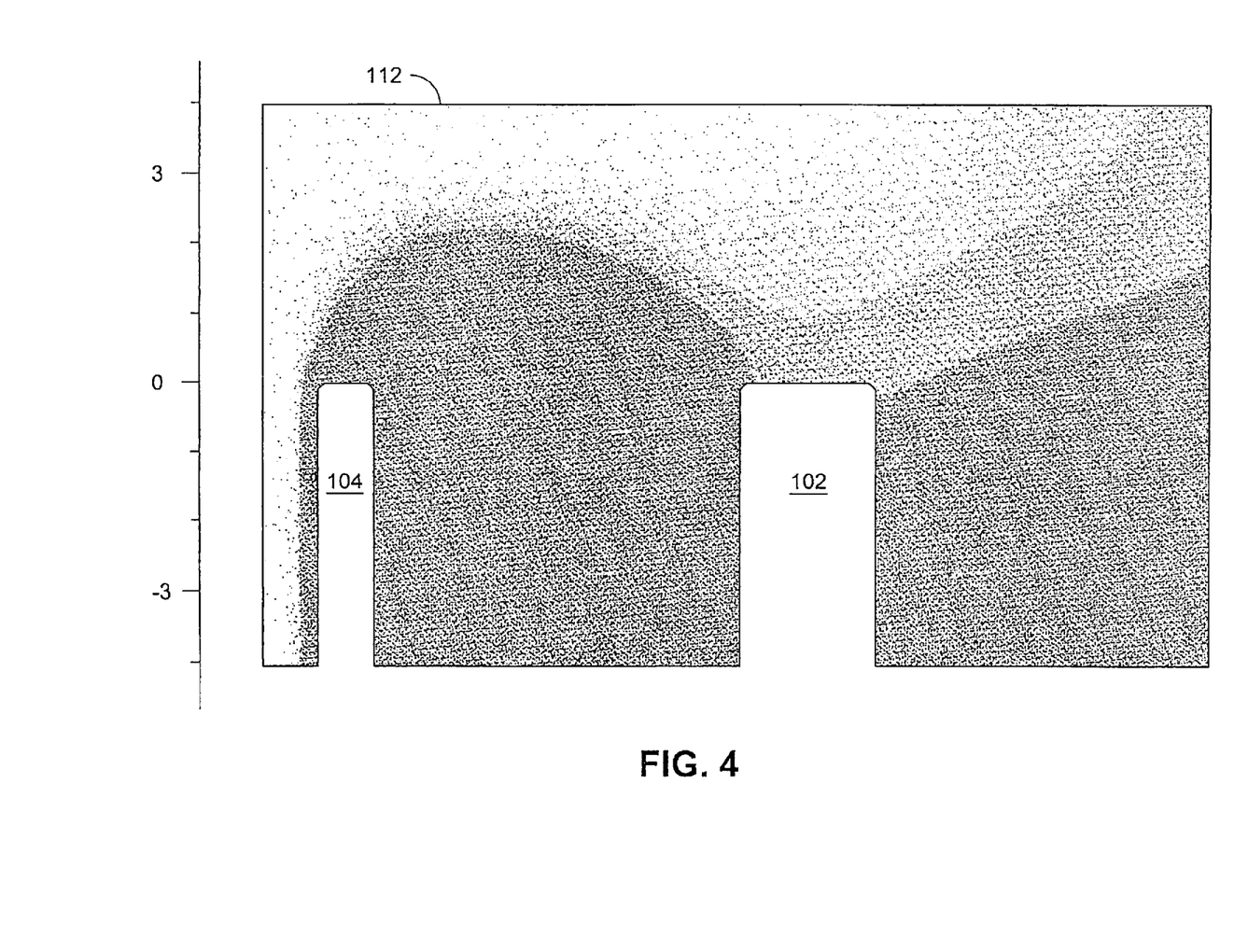
FIG. 4 is a diagrammatic view illustrating a concentration of analyte ions released by a sample on a surface upon interaction with the source ions in accordance with an example implementation of the present disclosure.

FIG. 4 shows a concentration of analyte ions released by a sample on surface 112 upon interaction with the source ions. In this embodiment, the analyte ions are sucked into the inner capillary 104. Because of the "inner racetrack effect" described above, the analyte ions end up in the center portion of the inner capillary 104 only. Ions reaching the wall of the inner capillary 104 tend to lose their charge and cannot be used for substance detection. In this case, a plug of analyte ions surrounded by clean gas may be referred to as a buffered plug of ions.

Figure 5:
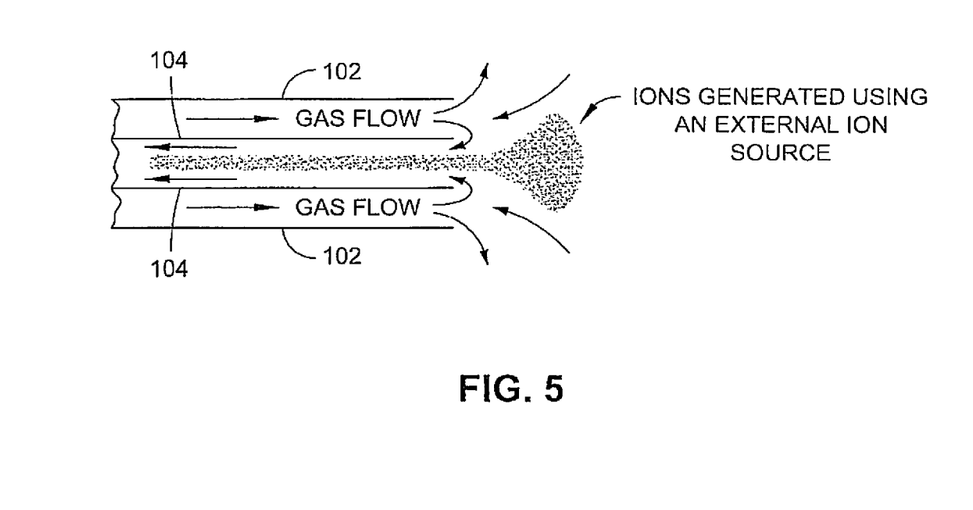
FIG. 5 is a partial diagrammatic cross-sectional view illustrating a concentric APCI surface ionization probe with ions generated using an external ion source in accordance with an example implementation of the present disclosure.

FIG. 5 illustrates an inner capillary 104 with sheath gas flow for use with a separate ion source (e.g., ions are not created using the concentric APCI surface ionization probe 100). In this case, gas flow from the outer tube 102 can be significantly smaller than the flow into the inner capillary 104 so that there is a net flow from the surrounding area to the inner capillary 104 but still enough flow to form a sheath gas close to the inside wall of the capillary.

Figure 6:
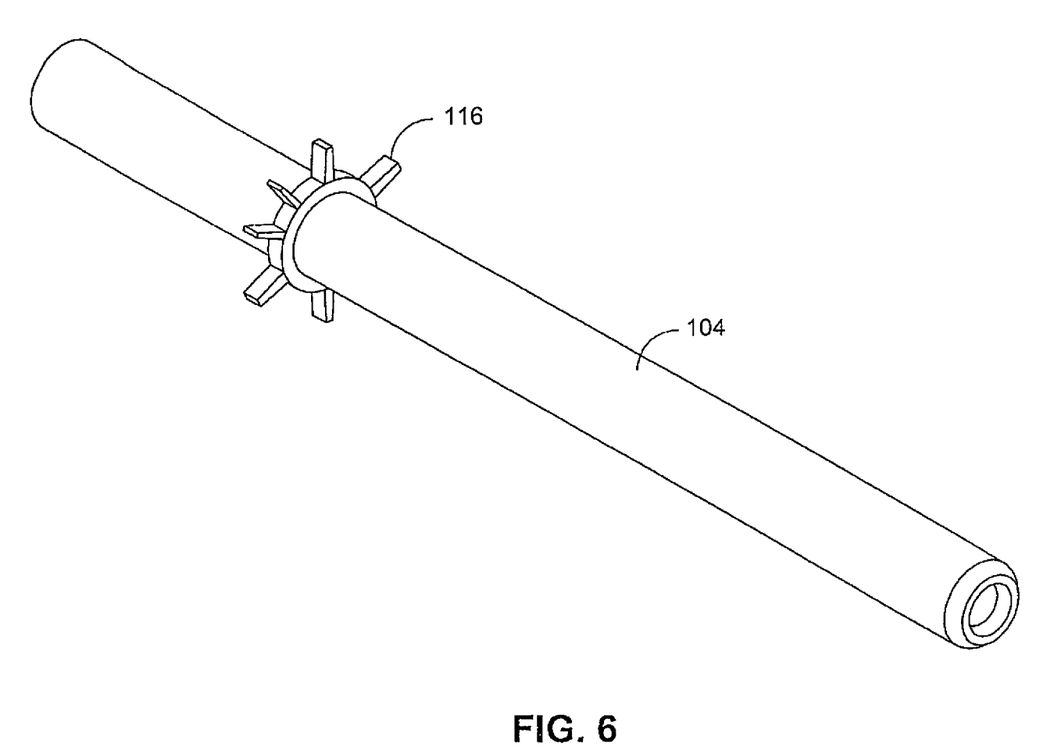
FIG. 6 is a partial diagrammatic cross-sectional view illustrating a concentric APCI surface ionization probe with an example inner needle probe in accordance with an example implementation of the present disclosure.
Figure 7:
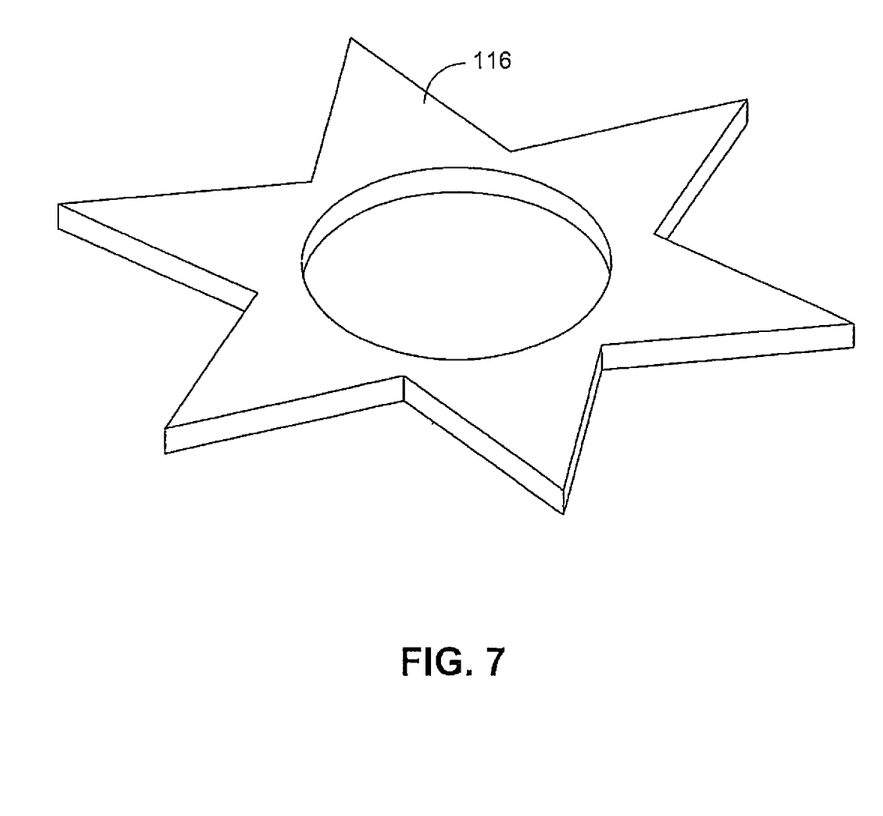
FIG. 7 is an isometric view illustrating an example inner needle electrode in accordance with an example implementation of the present disclosure.

FIG. 6 illustrates one embodiment of electrode geometry for generating ions proximate to position A2 shown in FIG. 3. In this embodiment, an electrode (e.g., inner needle electrode 116) may be included with inner capillary 104 for generating ions in the gas flow between the inner wall of the outer tube 102 and the outer wall of the inner capillary 104. The shape of the inner needle electrode 116 can be changed to include a number of radial spikes, such as those illustrated in FIG. 6. In some embodiments, the spikes can be as sharp as possible to maximize the electric field at the tip of the spike and cause minimal disturbance to the laminar gas flow inside the outer tube 102. In some implementations, more than one inner needle electrode 116 can be placed on the inner capillary 104. In some specific embodiments, the inner capillary 104 includes an electrical conducting material. In other specific embodiments, the inner capillary 104 is not an electrical conducting material. FIG. 7 illustrates one specific embodiment of an inner needle electrode 116 in the configuration of a star with six radial spikes.

Figure 8A:
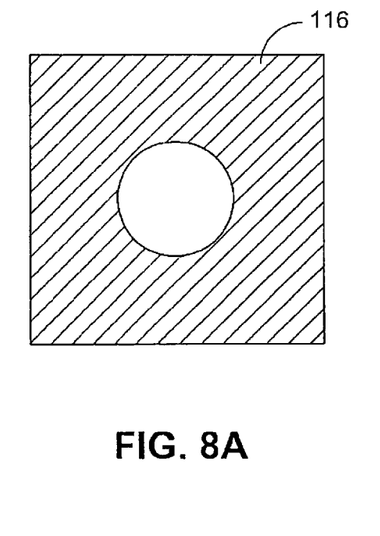
FIG. 8A is a cross-sectional view illustrating an example inner needle electrode in accordance with an example implementation of the present disclosure.
Figure 8B:
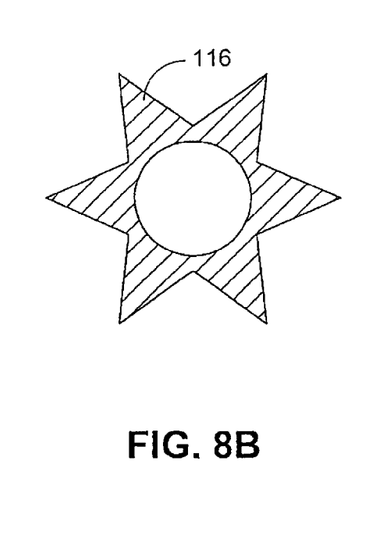
FIG. 8B is a cross-sectional view illustrating an example inner needle electrode in accordance with an example implementation of the present disclosure.
Figure 8C:
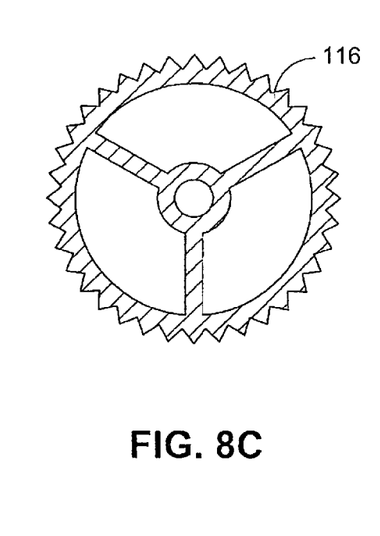
FIG. 8C is a cross-sectional view illustrating an example inner needle electrode in accordance with an example implementation of the present disclosure.

FIGS. 8A through 8C illustrate other specific embodiments of an inner needle electrode 116. In FIG. 8A, an inner needle electrode 116 in the configuration of a square with four radial corners is shown. In FIG. 8B, an inner needle electrode 116 in the configuration of a star with six radial spikes is shown. In FIG. 8C, an inner needle electrode 116 in the configuration of a gear is shown. The shape of the inner needle electrode 116 can include many other configurations as long as the configuration allows gas flow in the outer tube 102 close to the inner capillary 104 to pass without being ionized, and there is at least one sharp point or corner where an electric field is high enough to generate ions. In one specific embodiment, an aerodynamically configured inner needle electrode 116 allows for a substantially laminar gas flow in the outer tube 102, which can reduce mixing of the ionized gas flow and the clean (e.g., unionized) gas flow. In another specific embodiment, an inner needle electrode can include at least one protrusion in the shape of a single, double, triple, or higher order screw thread.

Figure 9:
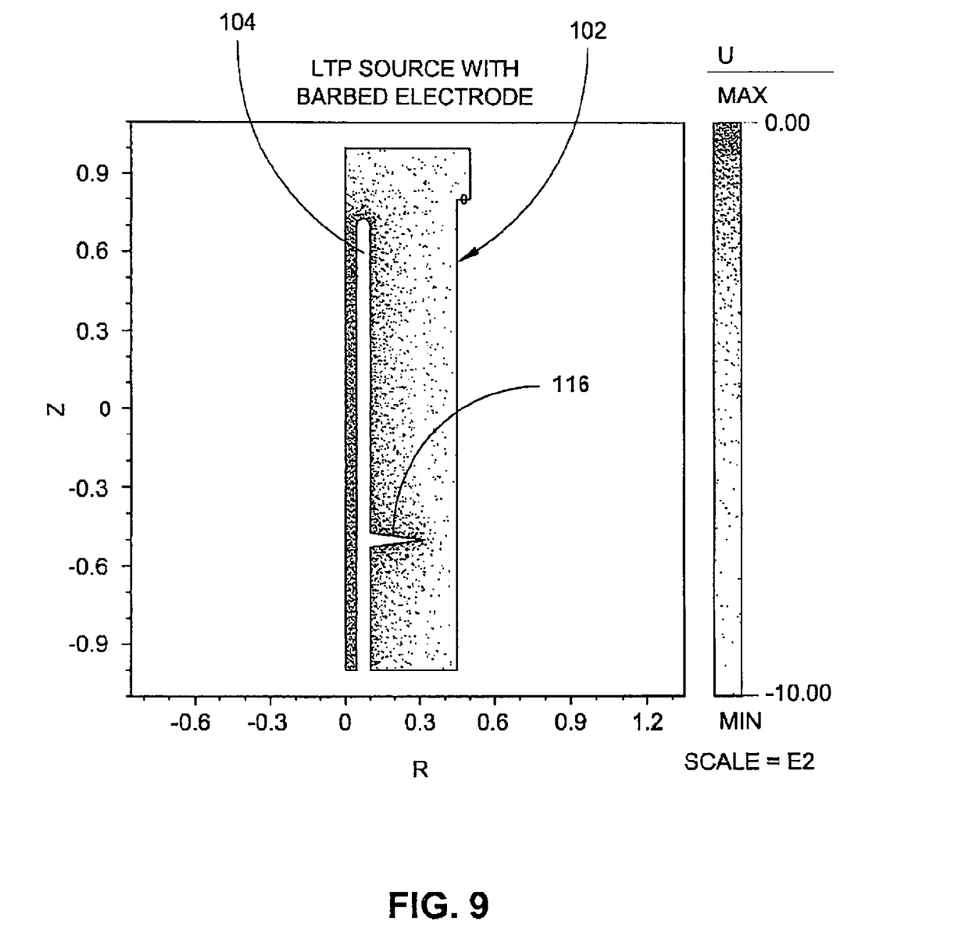
FIG. 9 is a diagrammatic view illustrating a potential distribution when a voltage is applied between the inner capillary with an inner needle electrode and an outer tube in accordance with an example implementation of the present disclosure.

FIG. 9 illustrates a potential distribution when a voltage is applied between the inner capillary 104 (e.g., first electrode 108) with an inner needle electrode 116 (i.e., represented by the spike in this embodiment) and an outer tube 102 electrode (e.g., second electrode 110). In this embodiment, the spike includes an inner needle electrode 116 in the configuration of a sharp-edged disk, and the potential is higher proximate to the inner needle electrode 116 and the inner capillary 104. With a concentric electrode geometry with spikes as described above, the electric field between the two electrodes does not transport the ions out of the tube, but the ions are transported out of the outer tube by an additional gas flow.

Figure 10:
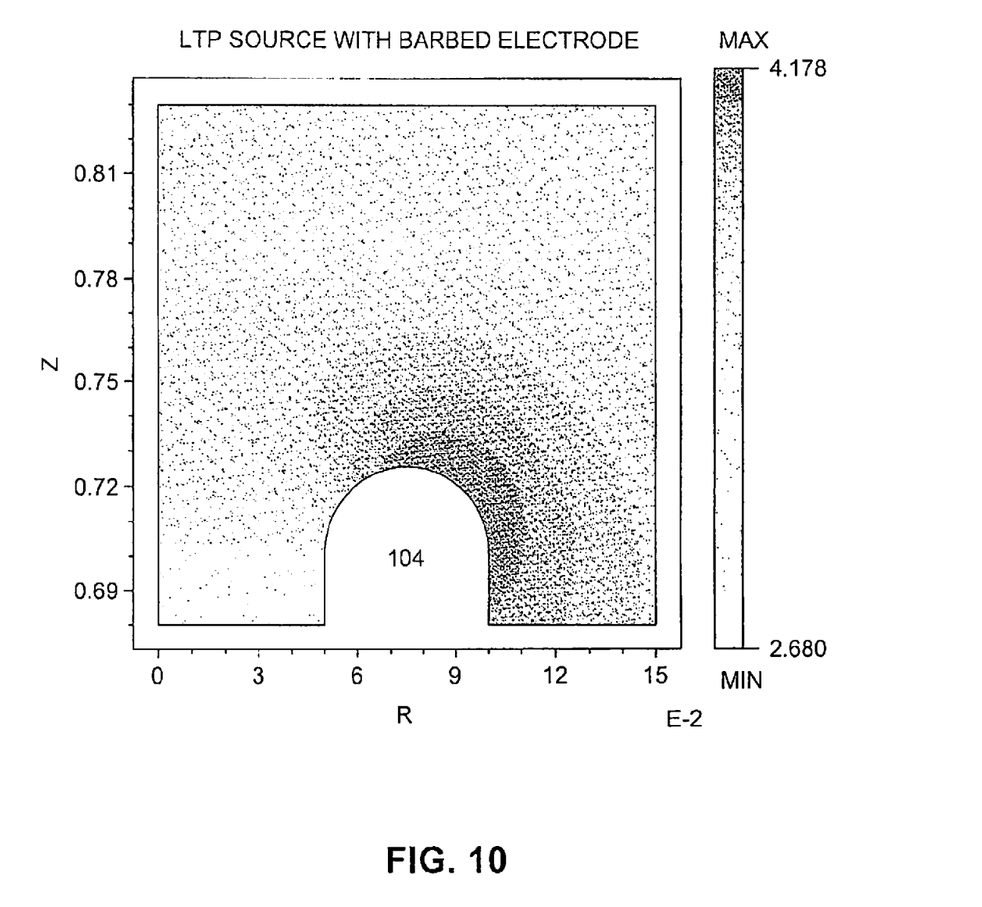
FIG. 10 is a diagrammatic view illustrating magnitude of the electric field at a rounded tip of the inner capillary in accordance with an example implementation of the present disclosure.

FIG. 10 illustrates magnitude of the electric field at a rounded tip of the inner capillary 104 (shown in logarithmic scale). In implementations, the roundness of the tip of the inner capillary 104 may be important to keep the electric field lower than the electric field at the inner needle electrode 116.

Figure 11:
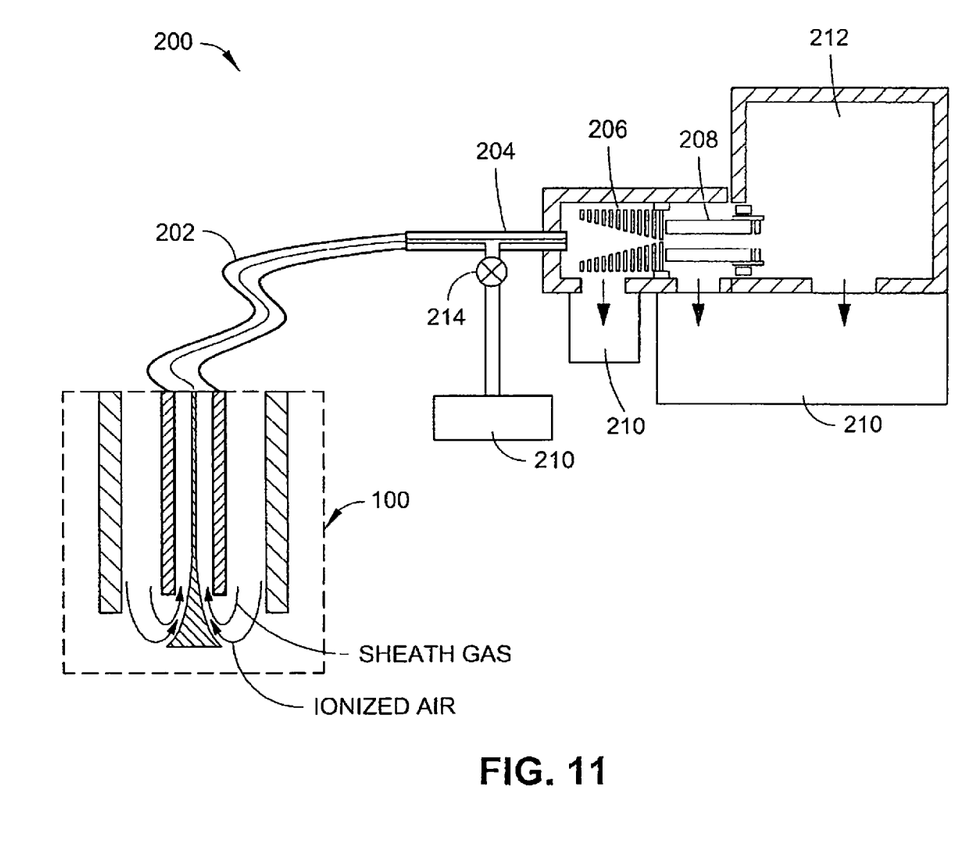
FIG. 11 is an environmental view illustrating a mass spectrometry system in accordance with an example implementation of the present disclosure.

As shown in FIG. 11, a mass spectrometry system 200 includes a concentric APCI surface ionization probe 100, a supersonic sampling tube 202, a heated capillary 204, an ion funnel 206, an ion guide 208, at least one pump 210, and/or a mass spectrometer 212. In implementations, a supersonic sampling tube 202 includes a tube configured for transporting a buffered plug of ions rapidly and efficiently from an ion source (e.g., the concentric APCI surface ionization probe 100) to a mass spectrometer 212. As a plug of ions travels down a sampling tube, ions may begin to diffuse and migrate toward the tube wall where they can neutralize and be lost for analysis. Use of a supersonic sampling tube 202 and/or a drop in pressure in the sampling tube 202 close to the ion source can prevent and/or minimize this neutralization of ions.

Figure 12:
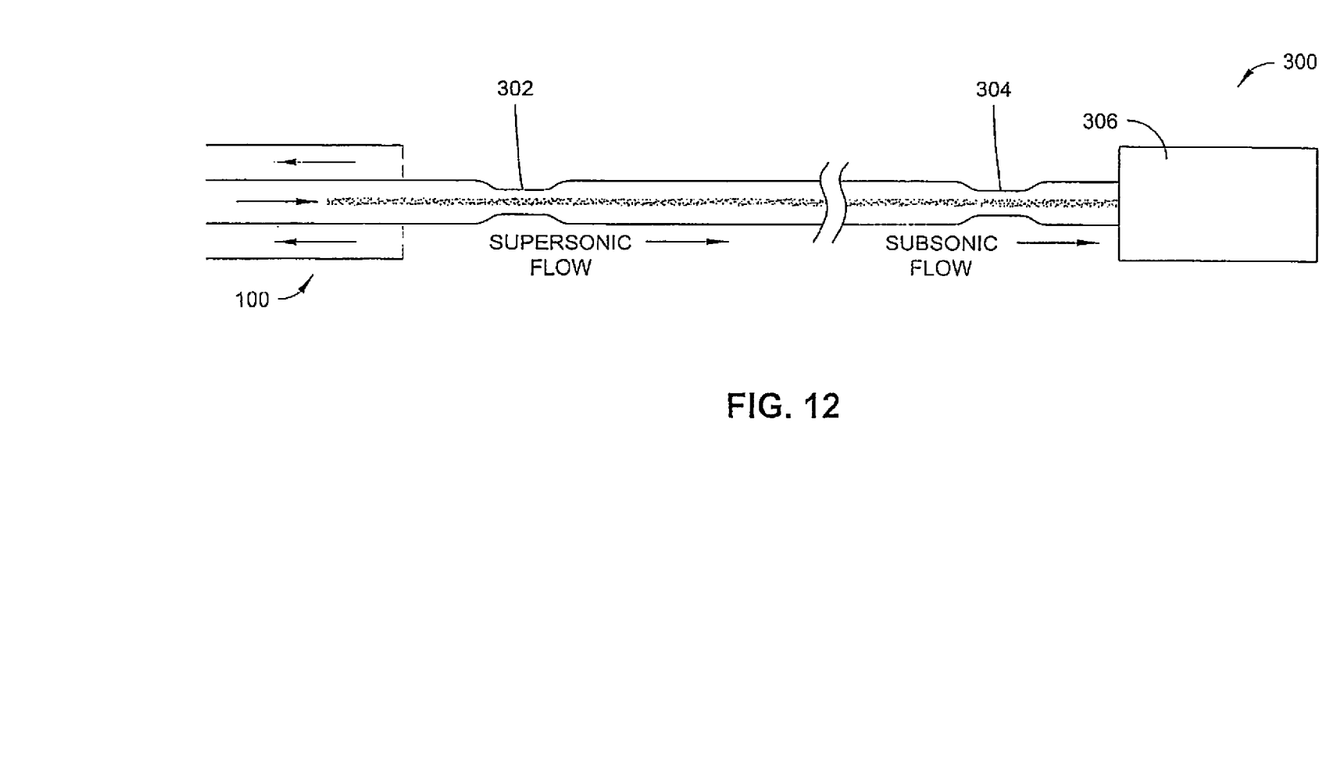
FIG. 12 is a partial cross-sectional view illustrating a supersonic sampling tube with a de Laval nozzle in accordance with an example implementation of the present disclosure.

As shown in FIG. 12, a supersonic sampling tube 202 includes a tube 300, a first de Laval nozzle 302, and may include a second de Laval nozzle 304. In an implementation using a supersonic sampling tube 202, a gas (e.g., air, etc.) flows from a high pressure atmosphere into the supersonic sampling tube 202 and pumped out the other end using a vacuum pump (e.g., pump 210). The pressure drop across the first de Laval nozzle 302 (e.g., proximate to the entrance portion of the supersonic sampling tube 202) as the gas flows causes the gas to expand and speed up to equal or greater than the speed of sound (Mach 1) at the narrowest position of the first de Laval nozzle 302. As the first de Laval nozzle 302 widens, the gas expands further and flow speeds greater than the speed of sound are reached. In order to obtain a flow as laminar as possible and keep energy losses to a minimum, smooth walls can be used for the supersonic sampling tube 202 (e.g., the supersonic sampling tube 202 may have a minimum radius of curvature). In an embodiment, a reverse process can be used at the low pressure end of the supersonic sampling tube 202 to bring the gas flow back below the speed of sound using a second de Laval nozzle 304 (e.g., a supersonic diffuser). In this embodiment, ions can be extracted from the subsonic ion flow using an electric field. In one specific embodiment, speed of the gas flow inside the supersonic sampling tube 202 can be greater than 500 m/s. In this specific embodiment, transfer of the gas down a 1 meter long tube will take approximately two (2) ms if the gas is not substantially slowed down by energy losses to the tube wall. In a specific embodiment, gas pressure, in an inlet tube 300 of approximately 1 mm and before a first de Laval nozzle 302 having a diameter of approximately less than 0.2 mm is approximately 760 Torr. Gas pressure after the first de Laval nozzle 302 can be approximately 100 Torr with a flow rate of approximately 0.6 slm.

In a second embodiment, the ratio of the length and width of the supersonic sampling tube 202 down-flow of the first Laval nozzle 302 can be made large enough that energy losses to the wall of the tube 300 slow the gas down to subsonic speeds (e.g., below Mach 1). In this embodiment, a second de Laval nozzle 304 may be omitted while ions are sampled from the subsonic gas flow.

As shown in FIG. 11, a mass spectrometry system 200 includes a heated capillary 204. In embodiments, mass spectrometry system 200 includes a heated capillary 204 disposed upstream of an entrance orifice. Utilizing a heated capillary 204 is one method used to limit the gas flow from the concentric APCI surface ionization probe 100 and supersonic sampling tube 202 into the vacuum system of a mass spectrometer 212. In embodiments, the heated capillary 204 may be heated to provide thermal energy to the solvated ions passing through them, thus desolvating these ions. In order for the sampling tube to function well (i.e. to keep the buffered plug of ions away from the wall), it is desirable to maintain a flow through the sampling tube 202 at all times. It is possible to achieve this flow while periodically reducing the amount of gas into the mass spectrometer by using an intermittent inlet. As shown, the intermittent inlet includes an extra pump 210 and valve 214, which are connected to the low pressure side of the sampling tube.

As shown in FIG. 11, a mass spectrometry system 200 includes an ion funnel 206. In implementations, an ion funnel 206 can include an assembly of parallel, coaxially arranged ring-shaped apertured diaphragms with tapering internal diameter separated by narrow intermediate spacers. In these implementations, the diameters of the apertures of the diaphragms gradually taper toward the central exit orifice of the ion funnel 206 into the subsequent chamber (e.g., ion guide chamber, mass analyzer system, etc.). The ion funnel 206 may function to focus an ion beam (or ion sample) into a small conductance limit at the exit of the ion funnel 206. In some embodiments, the ion funnel 206 operates at relatively high pressures (e.g., up to 30 Torr) and thus provides ion confinement and efficient transfer into next vacuum stage (e.g., an ion guide 208, mass spectrometer 212, etc.), which is at a relatively lower pressure. The ion sample may then flow from the ion funnel 206 into an ion guide 208 and/or mass spectrometer 212.

As shown in FIG. 11, a mass spectrometry system 200 includes an ion guide 208 adjacent to and downstream from the ion funnel 206. In some implementations, the ion guide 208 serves to guide ions from the ion funnel 206 into the mass spectrometer 212 while pumping away neutral molecules. In a specific embodiment, an ion guide 208 includes a multipole ion guide, which may include multiple rod electrodes located along the ion pathway where an RF electric field is created by the electrodes and confines ions along the ion guide axis. In some embodiments, the ion guide 208 operates at up to approximately 100 mTorr pressure, although other pressures may be utilized. Additionally, the ion guide 208 may be followed by a conductance limiting orifice, which may have a smaller diameter than the diameter of the exit orifice of the ion guide 208. In one specific embodiment, a low pressure end of the sampling tube 202 coupled to a mass spectrometer 212 can include an RF ion guide that is positioned close to the inner wall of the sampling tube 202. In a specific embodiment, the RF ion guide can include at least two conductors in the form of a double helix. In another specific embodiment, the RF ion guide can be integrated into the wall of the sampling tube. This RF ion guide can be configured such that ions and charged particles experience an average net motion away from the sampling tube 202 inner wall over the duration of an RF cycle.

As shown in FIG. 11, a mass spectrometry system 200 includes a pump 210, such as a low vacuum pump and/or a high vacuum pump. A vacuum, at least partially created by a low vacuum pump 210 (e.g., a diaphragm pump), may be necessary because it reduces and/or eliminates intermolecular collisions that would otherwise reduce the effectiveness of the mass spectrometry system 200 at separating elements based on their mass-to-charge ratios because molecular collisions may significantly alter the trajectories or ions involved and result in less ions reaching a detector (not shown). In embodiments, the vacuum pump 210 is coupled to at least one vacuum chamber of the mass spectrometry system 200. In some implementations, the vacuum pump 210 may include, for example, a scroll vacuum pump. In one specific embodiment, the vacuum pump 210 provides a vacuum of approximately up to 30 Torr (e.g., for a vacuum chamber that includes an ion funnel 206) although the pump(s) 210 may provide other vacuum pressures as well.

As shown in FIG. 11, a mass spectrometry system 200 includes a mass spectrometer 212. In implementations, a mass spectrometer 212 includes the component that separates ionized masses based on charge-to-mass ratios and outputs the ionized masses to a detector. Some examples of a mass spectrometer 212 include a mass analyzer, a time of flight (TOF) mass analyzer, a magnetic sector mass analyzer, an electrostatic sector mass analyzer, an ion trap mass analyzer, a portable mass spectrometer, etc. In another embodiment, a mass spectrometer 212 may include an ion trap device, which may include multiple electrodes that are used to trap ions in a small volume.

Figure 13:
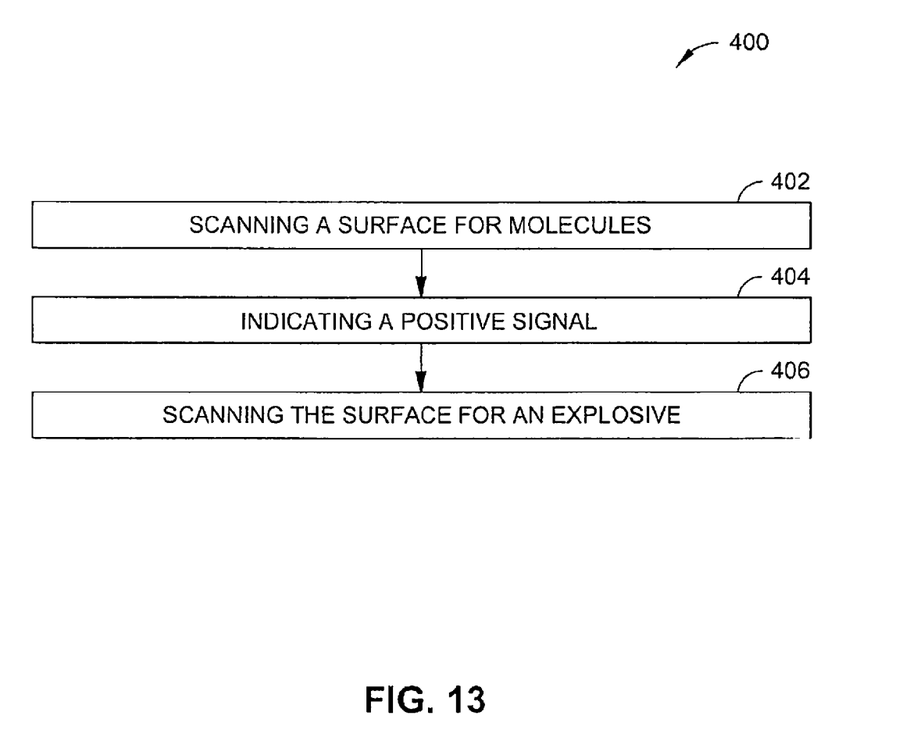
FIG. 13 is a flow diagram illustrating an example process for utilizing the concentric APCI surface ionization probe, supersonic sampling device, and mass spectrometry system illustrated in FIGS. 1 through 12.

FIG. 13 illustrates an example process 400 that employs the disclosed techniques to employ a concentric APCI surface ionization probe 100, a supersonic sampling tube 202, and/or a mass spectrometry system 200, such as the concentric APCI surface ionization probe 100, a supersonic sampling tube 202, and/or a mass spectrometry system 200 shown in FIGS. 1 through 12.

Accordingly, a surface is scanned for molecules indicating the presence of at least one fingerprint using a concentric APCI surface ionization probe (Block 402). In implementations, a surface 112 may be scanned at least 1-2 cm from the surface 112. However, the sensitivity of the concentric APCI surface ionization probe 100 increases if the probe can be brought in close proximity (2-3 mm) of the surface. In an implementation, a surface 112 is scanned for molecules indicating the presence of fingerprints, like lactic acid, lactate, or pyruvate, using a concentric APCI surface ionization probe 100 coupled to a mass spectrometry system 200. Fingerprints can be detected easily when the concentric APCI surface ionization probe 100 is kept approximately 2 cm from a smooth surface. Contaminated fingerprints are generally believed to be the main transfer mode of explosive traces and the like.

A positive signal is indicated when at least one fingerprint is detected (Block 404). In implementations, a sound can be made indicating the strength of the signal by volume or pitch in real time when a positive fingerprint signal is detected, helping the operator to move in the direction of the actual fingerprint. Once a fingerprint has been found, the concentric APCI surface ionization probe 100 and/or mass spectrometry system 200 can indicate the positive signal via a near real time light or sound from the concentric APCI surface ionization probe 100 and/or mass spectrometry system 200.

Then, a surface is scanned for at least one explosive using a concentric APCI surface ionization probe (Block 406). In implementations and during this second scan, one or more of the mass spectrometry system 200 and/or ion source parameters may be modified. Examples of parameters that can be modified include the APCI surface ionization gas temperature, addition of dopants, mass spectrometer mass range, etc. By showing that the signal of a sample 114 coincides with a fingerprint signal, the mass spectrometry system 200 can differentiate between substances present as a low, evenly distributed, background and substances from fingerprints. This differentiation becomes more relevant as common household chemicals become substances of interest because they are used for the fabrication of homemade explosives.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A method for using a concentric APCI surface ionization probe, comprising:
   detecting at least one area of interest by scanning a surface, using a concentric APCI surface ionization probe, for molecules indicating the presence of at least one indicator of the at least one area of interest;
   indicating a positive signal when the at least one area of interest is detected; and
   scanning the surface, using a concentric APCI surface ionization probe, for at least one explosive.

2. The method described in claim 1, where the signal indicating the at least one area of interest is converted to a visible or audible signal with an intensity, pitch or color that is a function of the signal intensity, so that the visible or audible signal can be used to direct the operator to move the probe towards the at least one area of interest.

3. The method described in claim 1, where the signal indicating the at least one area of interest and a signal of an analyte are combined to indicate that the position of the analyte coincides with the area of interest.

4. The method described in claim 1, where the area of interest is a fingerprint.

5. The method described in claim 4, where the fingerprint is made visible to indicate the person leaving a fingerprint in a position that coincides with an analyte of interest.

6. The method as described in claim 1, wherein scanning a surface comprises scanning for at least one of lactic acid, lactate, or pyruvate.

7. The method as described in claim 1, wherein during scanning of the surface using a concentric APCI surface ionization probe, the information contained in the signal indicating the at least one area of interest is used to modify at least ones of the following instrument parameters: a gas temperature, at least one gated discharge parameter, a presence of at least one dopant, or a mass spectrometer mass range.

* * * * *